US006787030B2

United States Patent
Hsi et al.

(10) Patent No.: US 6,787,030 B2
(45) Date of Patent: Sep. 7, 2004

(54) EFFLUENT COLLECTION APPARATUS AND METHOD

(75) Inventors: Kuo-Liang Hsi, Hayward, CA (US); Jindong Zhao, Beijing (CN); Michael Kochersperger, Belmont, CA (US); William E. Werner, San Carlos, CA (US); Pau-Miau Yuan, San Jose, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/602,342

(22) Filed: Jun. 23, 2003

(65) Prior Publication Data

US 2004/0060872 A1 Apr. 1, 2004

Related U.S. Application Data

(63) Continuation of application No. 09/885,292, filed on Jun. 19, 2001, now Pat. No. 6,582,597, which is a continuation of application No. 08/887,350, filed on Jul. 2, 1997, now Pat. No. 6,248,239.
(60) Provisional application No. 60/016,095, filed on Jul. 8, 1996.

(51) Int. Cl.[7] ............................................. B01D 15/08
(52) U.S. Cl. ..................... 210/198.2; 210/143; 210/656
(58) Field of Search ................................ 210/635, 656, 210/659, 198.2, 143; 422/70; 436/161; 73/61.56

(56) References Cited

U.S. PATENT DOCUMENTS

| | | | | |
|---|---|---|---|---|
| 4,631,122 A | * | 12/1986 | Pohl ........................ 204/299 R |
| 5,126,025 A | * | 6/1992 | Carson et al. ............ 204/180.1 |
| 5,520,817 A | * | 5/1996 | Anahara ...................... 210/656 |
| 5,674,388 A | * | 10/1997 | Anahara .................. 210/198.2 |
| 6,248,239 B1 | * | 6/2001 | Hsi et al. .................... 210/656 |

OTHER PUBLICATIONS

Cheng, Y. et al., "Membrane Fraction Collection for Capillary Electrophoresis," *Journal of Chromatography.* 608:109–116 (1992).*
Cheng, Y. et al., "Post–Capillary Immobiolon –P Membrane Fraction Collection for Capillary Electrophoresis," *Biotechniques.* 14:51–55 (1993).*
Cohen, S.A. et al., "Post–Run Analysis of Proteins Purified by Capillary Electrophoresis with Membrane Fraction Collection," *Techniques in Protein Chemistry V. Academic Press*, San Diego, pp. 293–302 (1994).*

(List continued on next page.)

*Primary Examiner*—Ernest G. Therkorn
(74) *Attorney, Agent, or Firm*—Vincent M Powers

(57) ABSTRACT

The present invention includes a method of analyzing one or more molecular components in a mixture of components. In the method, a mixture of molecular components, i.e., an analyte mixture, is separated on a capillary liquid chromatography column. The component-containing eluate from the column is deposited as a series of discrete, defined-volume microdrops, along a region of an adsorbent collection layer. During the chromatographic separation, the column eluate may also-be monitored to detect the presence of separated components in the equate. The one or more components deposited in the collection layer are then analyzed by selected analytical techniques. In related aspect, the invention includes a method of collecting one or more molecular components derived from a mixture of components, a blotter apparatus useful in the above method, and a system for analyzing one or more molecular components in a mixture of components.

4 Claims, 7 Drawing Sheets

OTHER PUBLICATIONS

Eriksson, K. et al., "Preparative Capillary Electrophoresis Based on Adsorption of the Solutes (Proteins) onto a Moving Blotting Membrane as They Migrate out of the Capillary," *Analytical Biology*. 201:211–215 (1992).*

Fernandez, J. et al., "Internal Protein Sequence Analysis: Enzymatic digestion for Less Than 10 μg of Protein Bound to Polyvinylidene Diflouride of Nitrocellulose Membranes," *Analytical Biochemistry*. 201:255 (1992).*

Grimm, R. and Harold, M., "Micropreparative Single Run Fraction Collection of Peptides Separated by CZE for Protein Sequencing," *Journal Cap. Elec.* 01:79:79–81 (1993).

Hawke, D.H. and Yuan, P–M., "S–Pyridylethylation of Cystine Residues," *Applied Biosystems User Bulletin* 28:1–8 (1987).

Hsi, K–L. et al., "A Practical Approach for Isolation and Characterization of Glycosylation Sites of Glycoproteins Bearing N–and/or O–Linked Carbohydrate Chains," *Techniques in Protein Chemistry IV*. pp. 143–1580 (1993).

Hsi, K–L. et al., "Development of a Capillary LC Blotting Systems for Low and Sub–Picomole Sequecing Sample Prepartion," *Protein and Peptides Lett.* 4(1):1–8 (1997).

Kochersperger, M.L. et al., Abstract No. 265–M, *Protein Science*. 3(1):98 (1994).

Konse, T. et al., "Blotting Membrane Micropreparation in Capillary Electrophoresis to Evaluate Enzyme Purity and Activity," *Analytical Biochemistry*. 214:179–181 (1993).

Murata, H. et al., "On–Line Membrane Blotting of Peptides and Proteins for a Capillary Column," *Analytical Biochemistry*. 210:206–208 (1993).

Spellman, W.M. et al., "Carbohydrates Structures of Human Tissue Plasminogen Activator Expressed in Chinese Hamster Ovary Cells," *Journal of Biol. Chem.* 264(24):14100 (1989).

Warren, W.J. et al., "Protein Immunodetection Using Capillary Electrophoresis with Membrane Fraction Collection," *LC–GC Magazine*. 12:22–28 (1994).

Werner, W.E. et al., "A New Sample Preparation Device for Protein/Peptide Sequencing," Abstract No. 505–M, *Protein Science*. 4(2):150 (1995).

* cited by examiner

* Dye marks *

EFFLUENT COLLECTION APPARATUS AND METHOD

CROSS-REFERENCE TO RELATED APPLICATIONS

This application is a continuation of U.S. application Ser. No. 09/885,292, filed Jun. 19, 2001, now U.S. Pat. No. 6,582,547, which is a continuation of U.S. application Ser. No. 08/887,350, filed Jul. 2, 1997, now U.S. Pat. No. 6,248,239 which claims priority under 35 U.S.C. 120 to provisional patent application No. 60/016,095, filed Jul. 8, 1996, all of which are incorporated herein by reference.

FIELD OF THE INVENTION

The present invention relates to methods of fractionating and collecting analytes. In one embodiment, the invention relates to an improved method for collecting chromatographically separated analytes such as polypeptides, polynucleotides, and polysaccharides.

REFERENCES

Fernandez, J., et al., *Anal. Biochem.* 201:255 (1992).

Hawke, D. H. and Yuan, P-M, *Applied Biosystems User Bulletin* 28:1–8 (1978, 1988).

Kochersperger, M. L., et al., *Protein Science* 3:Suppl. 1 98, 265-M (1994).

Kuo-Liang Hsi, et al., in *Techniques in Protein Chemistry IV* pp. 143–150 (1993).

Sambrook, J., et al., *Molecular Cloning, 2nd Ed.*, Cold Spring Harbor Laboratory Press (1989).

Murata, H., et al., *Anal. Biochem.* 210:206 (1993).

Spellman, W. M., et al., *J. Biol. Chem.* 264:14100 (1989).

BACKGROUND

Purification and characterization of chemical analytes such as polypeptides, polynucleotides, and polysaccharides, have become increasingly important in the chemical and medical arts. Numerous analytical methods have been developed for a variety of purposes, such as testing for the presence of biological contaminants or toxins, identifying new components in biological systems, and verifying sample purity, for example. Often, analytes of interest are available only in trace amounts or at very low concentrations. Accordingly, there has been much interest in developing analytical techniques with increased sensitivity to facilitate characterization of such analytes.

For many applications, one or more purification steps are necessary before the analyte(s) of interest can be detected or quantified. In the case of analytes which are present in trace amounts, purification has proved difficult for a number of reasons. For example, when analytes elute closely together under given separation conditions, it has been difficult to collect adjacent peaks in a manner that retains resolution, i.e., without significantly diminishing the resolution achieved by the selected purification method. Such small-sample purifications have also been hampered by low sample recoveries due to dilution or adherence of sample on collection vessel surfaces.

Although fraction collection using individual collection vessels has been the traditional mode for collecting and storing resolved sample components, this approach has generally been unsuitable for small sample amounts because of low recoveries as above. Accordingly, other collection methods have been proposed.

One proposed approach involves collecting eluted samples on an adsorbent surface by continuously dragging the outlet of a chromatography column across an adsorbent surface, such that the column effluent is continuously dispensed onto the adsorbent in a continuous trail. Such a method has been proposed by Murata et al. (1993) for collecting polypeptides from a capillary liquid chromatography column. In their method, a pen-holding device is used to maintain the column outlet in continuous contact with a collection membrane.

Although such dragging methods have allowed relatively simple apparatus design, subsequent experience has shown that the fluid outlet often snags on the adsorbent surface, leading to tearing or gouging of the surface or, conversely, locking of the outlet onto the surface so that the outlet cannot move or the adsorbent moves with the outlet. Temporary catching of the outlet on the membrane can lead to discontinuities and other irregularities in the deposited sample, so that the locations of resolved peaks do not correspond with the true elution profile. Tearing or gouging can seriously hinder sample recovery. Long-term locking between the surface and the outlet can result in superimposition of some or all of the resolved peaks, defeating the purpose of the separation. Yet another drawback of the dragging method is the possibility of cross-contamination of eluate due to carry-over of liquid between the capillary outlet and the adsorbent collection layer.

It would be desirable to provide an apparatus and method for collecting small amounts of eluted sample components with high sample recovery, while avoiding the problems mentioned above. In particular, it would be desirable to provide such a method for collecting separated sample components in a manner that allows immediate use or long-term storage for subsequent analysis.

SUMMARY OF THE INVENTION

The present invention is directed, in one aspect, to a method of analyzing one or more molecular components in a mixture of components. In the method, a mixture of molecular components, i.e., an analyte mixture, is separated on a capillary liquid chromatography column. The component-containing eluate from the column is deposited as a series of discrete, defined-volume microdrops, along a region of an adsorbent collection layer. During the chromatographic separation, the column eluate may also be monitored to detect the presence of separated components in the eluate. The one or more components deposited in the collection layer are then analyzed by selected analytical techniques.

In one embodiment of the method, the collection layer is immobile during the depositing step, and the depositing step includes reciprocating a deposition head, for depositing the eluate on the collection layer, toward and away from a position of contact with the collection layer, while the deposition head is moved laterally relative to the collection layer. In a preferred embodiment, the deposition head is moved laterally over the collection layer in a linear direction. In an alternative embodiment, the depositing step includes reciprocating a deposition head toward and away from a position of contact with the collection layer while the collection layer is moved laterally relative to the deposition head.

In related aspect, the invention includes a method of collecting one or more molecular components derived from a mixture of components. In the method, a mixture of molecular components is separated on a capillary liquid chromatography column. The component-containing eluate from the column is deposited as a series of discrete, defined-volume microdrops along a region of an adsorbent collection layer. The collected components in the collection layer may then be analyzed by selected analytical techniques.

In another aspect, the invention includes a blotter apparatus which is useful in the methods described above. The apparatus includes an adsorbent collection layer, and means for depositing component-containing eluate from a capillary liquid chromatography column as a series of discrete, defined-volume microdrops, along a region of the adsorbent collection layer. In one embodiment, the apparatus further includes means for monitoring the column eluate to detect the presence of separated components in the eluate, and a control unit operatively connecting the monitoring and depositing means for controlling the flow rate and volume of deposited microdrops. As described above, the collection layer may be immobile, and the depositing means includes a deposition head which is capable of reciprocating toward and away from a position of contact with the collection layer while the deposition head is moved laterally relative to the collection layer. In an alternative embodiment, the deposition is immobile with respect to lateral movement, and the apparatus includes means for moving the deposition layer laterally relative to the deposition head.

The invention also includes a system for analyzing one or more molecular components in a mixture of components. The system includes (i) a capillary liquid chromatography column, (ii) means supplying liquid to the column at a selected flow rate, (iii) means for monitoring the column eluate to detect the presence of separated components in the eluate, (iv) means for depositing component-containing eluate from the column as a series of discrete, defined-volume microdrops, along a region of an adsorbent collection layer, and (v) a control unit operatively connecting the monitoring and depositing means for controlling the flow rate and volume of deposited microdrops.

In one embodiment, the depositing means includes (i) a stage adapted to support the adsorbent collection layer, (ii) a deposition head operable to reciprocate toward and away from a position of contact with the collection layer, and (iii) means for moving the stage and head laterally with respect to one another.

In one embodiment, the stage is effective to hold the collection layer immobile, and the depositing means includes means for moving the deposition head laterally with respect to the collection layer. In an alternative embodiment, the deposition head is immobile with respect to lateral movement, and the system further including means for moving the stage laterally with respect to the deposition head.

The control means may be operable to change the deposition rate and microdrop deposition volume in response to different peak patterns detected by the monitoring means.

These and other objects and features of the invention will be more apparent from the following detailed description when read in light of the accompanying drawings.

DETAILED DESCRIPTION OF THE INVENTION

I. Definitions

The following terms as used herein are intended to have the following meanings unless the context indicates otherwise.

"Capillary liquid chromatography" or "cLC" refers to low and high pressure chromatographic methods in which the chromatography column and associated tubing for transporting solvents and eluate are of small internal cross sections, typically of 1 mm or less, more typically less than 200 $\mu$m, and preferably less than 100 $\mu$m.

II. Apparatus

In one aspect, the invention includes a blotter apparatus useful for collecting one or more chromatographically separated molecular components from a mixture of components. The apparatus includes an adsorbent collection layer, and means for depositing component-containing eluate from a capillary liquid chromatography column as a series of discrete, defined-volume microdrops, along a region of the adsorbent collection layer.

Figure 1:
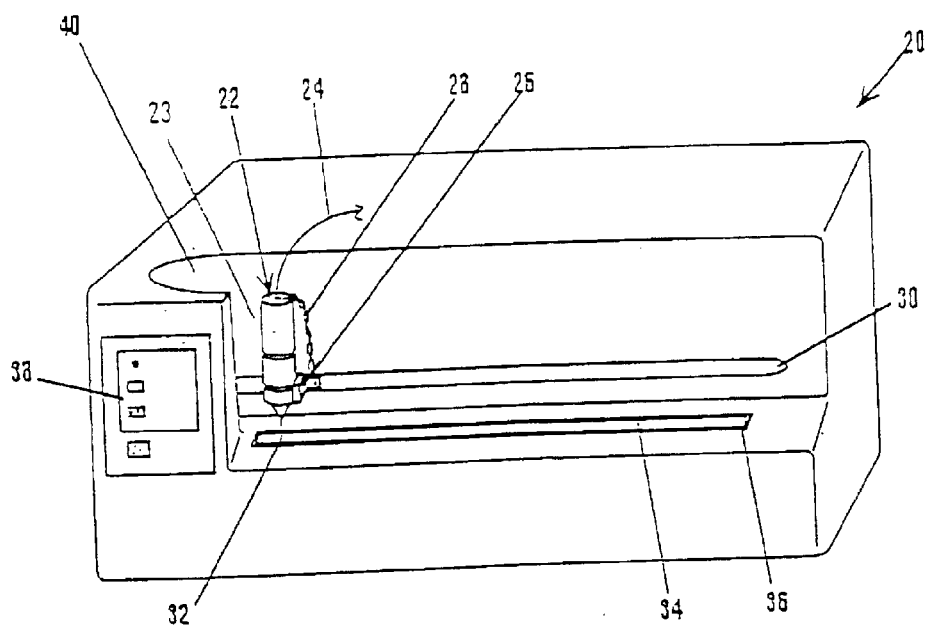
FIG. 1 shows a simplified schematic view of a blotting apparatus which may be used in practicing the invention.

FIG. 1 illustrates an exemplary blotter apparatus 20 for use in the invention. Apparatus 20 includes means 22 for depositing eluate from a capillary liquid chromatography (cLC) column onto an adsorbent collection layer 34. As illustrated in the figure, depositing means 22 is a deposition head which includes a "push-pull" solenoid element 23, and passing through the head, outlet region 24 of the cLC column. The "push-pull solenoid" is also referred to herein as "means capable of reciprocating toward and away from a position of contact with the collection layer". The deposition head is carried by arm 26 which protrudes out of slot 30, for laterally moving the deposition head over the collection layer. Lateral movement of arm 26 may be achieved using a stepper motor assembly (e.g., screw-type) according to mechanisms known in the art.

Electrical signals from a controller (not shown) for reciprocating the head towards and away from the adsorbent layer are transmitted to the solenoid element via electrical connection 28. Through the reciprocating action of the head, cLC outlet end 32 is brought into contact with collection layer 34 to deposit the eluate as a series of discrete, defined-volume microdrops along a region of collection layer 34.

The apparatus further includes a sample tray 36, which may be referred to as a "stage adapted to support the adsorbent collection layer", and which fits snugly in a complementary cavity which holds the tray and adsorbent immobile during operation. The sample tray, adsorbent layer, and deposition head are also encompassed by the term "means for moving the stage and head laterally with respect to one another."

With continued reference to FIG. 1, the apparatus further includes a control panel 38 for setting the lateral speed of the deposition head and optionally, the rate of reciprocation of the head. The apparatus may also include a recess region 40 for storing the head in a non-exposed "home position" when eluate is not being collected.

Figure 2:
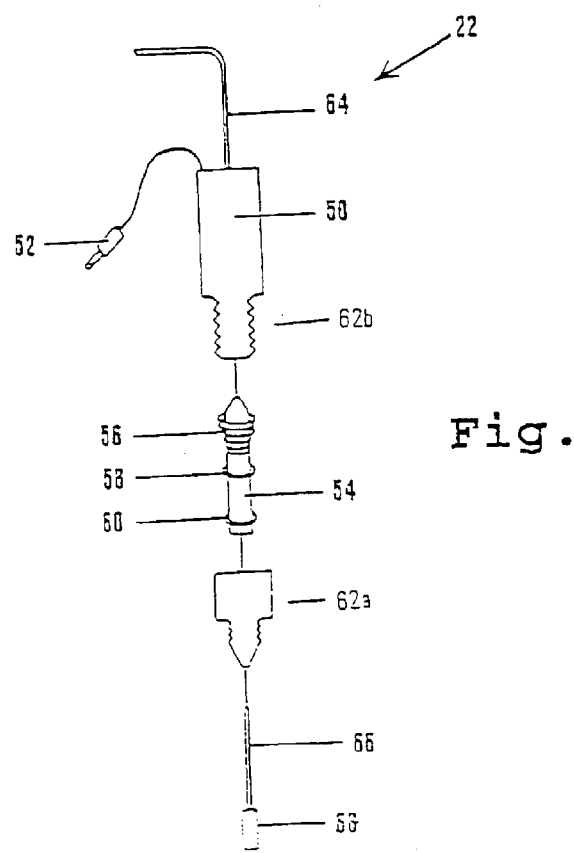
FIG. 2 shows an exploded view of a dynamic blotter element for raising and lowering the outlet end of a capillary tube above the surface of an adsorbent collection layer.

A depositing means 22 in accordance with FIG. 1 is illustrated in further detail in FIG. 2. Depositing means 22 includes a solenoid 50 equipped with an electrical connection 52 for delivering current to the solenoid. Solenoid 50 further defines a hollow cylindrical region along and coaxial with its longitudinal axis for receiving core 54.

Core 54 includes a wire spring 56, washer 58, and C-ring 60, which are fitted around the core to provide a spring mechanism as described further below. The core 54 and its elements 56, 58 and 60 are enclosed by means of a bushing 62a having an internal female screw-type fitting (not shown) for snugly engaging a corresponding male fitting 62b on the lower portion of solenoid 50.

Capillary outlet region 64 (corresponding to outlet region 24 in FIG. 1) passes through the longitudinal axes of solenoid 50, core 54, and bushing 62a so that capillary outlet end 66 extends through the bottom of bushing 62a. Outlet region 64 is snugly held by the interior of core 54, but not by solenoid 50 or bushing 62a. This allows the vertical motion of capillary outlet end region 66 to be controlled by the vertical movement of the core within the confines of the solenoid and bushing. It will be appreciated that although capillary outlet region 64 is shown as passing through the center of the deposition head, the outlet may be located elsewhere on the deposition head, e.g., on the exterior of the solenoid element with appropriate linkage to core 54 to achieve controlled vertical movement of the outlet.

Outlet end 68 is capped snugly with a sleeve 68, preferably made of "TEFLON", which is made flush with the tip of outlet end 66. Sleeve 68 helps maintain the eluate in the region immediately below the tip by preventing the eluate from climbing up the outside of the outlet end and disrupting fluid flow. The sleeve is also effective to cover the sharp edges of the capillary tip so as to shield the adsorbent layer from potential snagging or tearing. A further advantage of the sleeve is that the sleeve increases the effective cross-section of the capillary outlet so that the impact of the outlet on the adsorbent layer is dampened, preventing puncture of the adsorbent layer.

When fully assembled, deposition head 22 can reciprocate between two positions designated here as the extended position (contact with the adsorbent layer) and the retracted position (no contact with the adsorbent layer). In the resting state, i.e., when no current is supplied to the solenoid, deposition head 22 occupies the extended position due to the pushing force of spring 56 acting against the tip of male fitting 62b. When the head is positioned over the adsorbent collection layer, outlet end 66 and sleeve 68 are brought into contact with the adsorbent layer. Upon contact, any eluate that has collected beneath the tip of outlet end 66 is deposited onto, and adsorbed by, the collection layer.

It will be appreciated that the force with which the tip of the outlet contacts the adsorbent collection layer can be adjusted and minimized by suitable choice of spring stiffness, and by positioning the deposition head relative to the surface of the adsorbent collection layer so that the capillary outlet tip only gently touches the adsorbent layer when the head is in the extended (contact) position. As noted above, the impact of the outlet tip on the collection layer is further softened by the presence of sleeve 68. During contact with the adsorbent layer, the eluate is drawn from the tip into the adsorbent layer.

The deposition head is moved to the retracted position by passage of current through solenoid 50 via connection 52. The magnetic field generated in the interior of the solenoid draws core 54 upward toward the solenoid, so that outlet 66 is lifted away from the collection layer. During the time the head is in the retracted position, eluate collects under the tip of capillary outlet region 66 until the next time the tip is contacted with the adsorbent layer.

Figure 3:
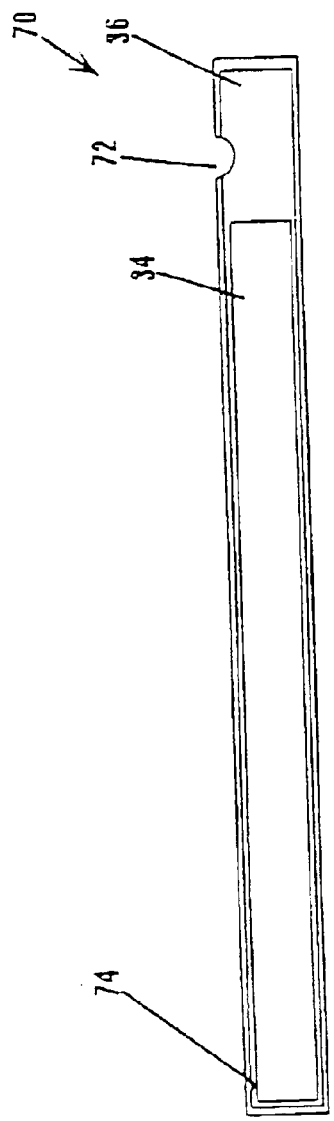
FIG. 3 shows an overhead view of a tray assembly for use in the blotter apparatus of the invention.

FIG. 3 illustrates a linear adsorbent layer and tray assembly (i.e., a stage adapted to support the adsorbent collection layer) which may be used in the apparatus of FIG. 1. Assembly 70 includes an adsorbent layer 34 which is held in a shallow depression (not shown) provided by tray 36, which immobilizes the layer from lateral movement. The assembly further includes a positioning notch 72 which interlocks with a corresponding protrusion in the blotter apparatus to ensure proper orientation. The tray may also include a mark 74 which indicates the start site for sample collection from the deposition head. Alternatively, the adsorbent layer may include such a mark if desired. For the device described in the Example section below, the overhead dimensions of the adsorbent layer were approximately 1.8 mm×200 mm. Of course, these dimensions are merely illustrative.

The adsorbent collection layer is formed of any adsorbent material appropriate for the analyte of interest. Where the analyte is a protein, the adsorbent is preferably one which binds protein with a strong affinity. Exemplary adsorbent materials include polyvinylidene difluoride (PVDF), nitrocellulose, and various other membranes in the Immobilon series available from Millipore (Bedford, Mass.). For binding of polynucleotides, nitrocellulose and nylon are useful, for example (e.g., available from Schleicher & Schuell, Keene, N.H.). The collection layer may also have additional layer underneath the layer which contacts the capillary outlet, to help draw the eluate solvent into the collection layer.

The rate of lateral movement of the deposition head with respect to the adsorbent layer, the frequency of contact, and the durations of contact and non-contact between the capillary outlet and adsorbent layer will depend on various factors, such as the flow rate of eluate, the degree of resolution of sample components to be collected, the amount of the components, and the absorptive capacity of the adsorbent layer. For capillary liquid chromatography, flow rates are generally between 1 and 100 $\mu$L/min, and preferably between 1 and 10 $\mu$L/min. In the examples described below, the contacting cycle time was 2 seconds per cycle, with a contact time of 1.8 seconds and a non-contact time of 0.2 seconds. The lateral speed of the deposition head relative to the adsorbent layer was 1 mm/min. At a flow rate of 4 $\mu$L/min, with 30 contact cycles per minute, the volume of eluate deposited per contact cycle was about 130 nL, with a density of 4 $\mu$L deposited per mm of adsorbent. It will be appreciated that other deposition rates and lateral speeds may be used, according to the requirements of the particular sample and separation conditions.

While the arrangement of the adsorbent layer and deposition pen are shown with regard to a particular embodiment in FIGS. 1 to 3 (lateral movement of a reciprocating deposition head in a linear direction over an immobile adsorbent layer), it will be appreciated that other configurations can also be used. For example, a reciprocating deposition head can be positioned at the end of an arm which rotates about an axis perpendicular to the plane of the adsorbent layer. In this configuration, the eluate is collected in a circular or arc shaped pattern. When eluate can also be collected in a spiral pattern on the adsorbent layer when the apparatus includes means for shortening the length of the holding arm.

In an alternative embodiment, the reciprocating deposition may be held immobile with respect to lateral movement, and the apparatus includes means for moving the adsorbent layer laterally relative to the deposition head. In one embodiment, the adsorbent layer can be moved laterally with respect to the deposition head by means of a take-up wheel which pulls the adsorbent layer past the head, where axis of rotation of the wheel is perpendicular to the longitudinal axis of the deposition head and parallel to the surface of the adsorbent layer. Alternatively, the apparatus includes means for rotating the adsorbent layer about an axis parallel to the longitudinal axis of the deposition head, so that the eluate is collected in a circular or arc-shaped pattern. Other configurations are also possible.

In an alternative embodiment, the depositing means of the apparatus is immobile with respect to vertical movement (movement in a direction toward and away from the adsorbent layer), and contact between the capillary outlet and the adsorbent layer is accomplished by reciprocating movement of the adsorbent layer toward and away from a position of contact with the capillary outlet of a nonreciprocating head. In one embodiment, the apparatus includes means for moving the adsorbent layer in a reciprocating fashion toward and away from the deposition head, as just mentioned, and also means for moving the adsorbent layer laterally with respect to the adsorbent layer. Alternatively, the apparatus includes means for moving the adsorbent layer in a reciprocating fashion with respect to a nonreciprocating deposition head, and means for moving the deposition head laterally with respect to the adsorbent layer along the lines discussed above.

In a further embodiment, the apparatus includes means for monitoring the column eluate to detect the presence of separated components in the eluate, and a control unit operatively connecting the monitoring and depositing means for controlling the flow rate and volume of deposited microdrops. The monitoring means include a detector which is selected according to the signal of the sample components to be detected, as discussed further below. Typical detection methods include UV-visible absorption, fluorescence, chemiluminescence, CCD, radioisotopic detection, and ionization detection (electrical conductance), for example.

III. Collection System

The invention also includes a system for analyzing one or more molecular components in a mixture of components. The system includes (i) a capillary liquid chromatography (cLC) column, (ii) means supplying liquid to the column at a selected flow rate, (iii) means for monitoring the column eluate to detect the presence of separated components in the eluate, (iv) means for depositing component-containing eluate from the column as a series of discrete, defined-volume microdrops, along a region of an adsorbent collection layer, and (v) a control unit operatively connecting the monitoring and depositing means for controlling the flow rate and volume of deposited microdrops.

Figure 4:
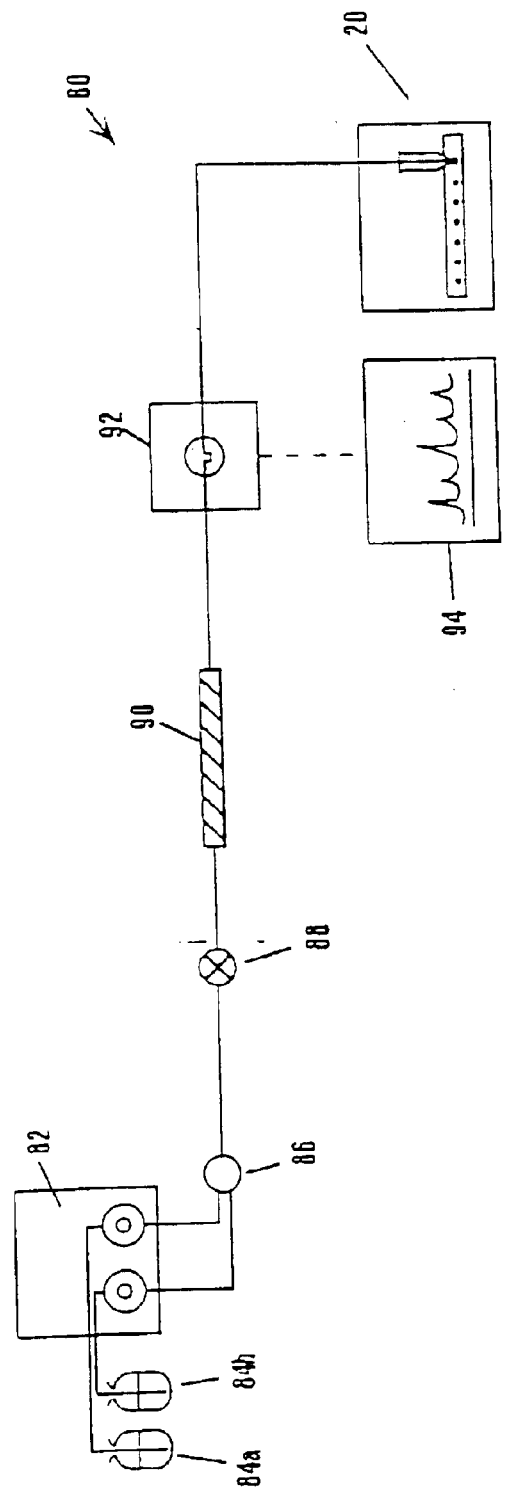
FIG. 4 shows schematically a blotting system in accordance with the present invention.

FIG. 4 illustrates an exemplary system 80 in accordance with the invention. System 80 includes solvent pump means 82 which draws solvent from reservoirs 84a and 84b at selected flow rates and ratios, and which are mixed together by mixer 86. The system also includes a sample injector 88 equipped with a sample loop, vent, and waste lines as conventional for cLC. Pump means 82 and reservoirs 84a, 84b are collectively referred to as "means for supplying liquid to the cLC column at a selected flow rate". The sample injector is connected by suitable tubing connections to cLC column 90. Eluate from column 90 passes through detector 92, whose signal output is displayed on a chart recorder 94 (or equivalent display device). Eluate exiting from the detector is fed to a depositing means or blotter apparatus 20.

The depositing means 20 preferably includes (i) a stage adapted to support the adsorbent collection layer, (ii) a deposition head operable to reciprocate toward and away from a position of contact with the collection layer, and (iii) means for moving the stage and head laterally with respect to one another. These features are substantially as described above with respect to the various depositing means described in section II.

The cLC column, pump means, solvents, and solvent gradient are selected according to the analyte components to be collected.

The cLC column used in the system may be any cLC column available in the art. A large variety of cLC columns are available from numerous commercial suppliers, including J&W Scientific, Micro-Tech Scientific, Interchim, Alltech, Supelco, Hewlett-Packard, and others. The column may contain any suitable solid phase, such as normal phase (e.g., silica gel), reversed phase (e.g., C-18 or C-8 derivatized supports), hydrophobic interaction, cation and anion exchange resins, immobilized antibody affinity columns, and the like. The columns are usually smaller than standard LC columns, typically having inner diameters of 0.2 to 1.0 mm and lengths of 5 to 25 cm, although columns having dimensions beyond these ranges are also contemplated.

For charged analytes such as polynucleotides and proteins, anion or cation-exchange solid supports may be used, where elution is via salt gradient or change in pH. Alternatively, reversed-phase supports are also effective, where elution is accomplished using a gradient of increasing or decreasing organic solvent concentration, usually in the presence of an ion-pairing reagent such as TFA (trifluroacetic acid) or various ternary or quaternary amine compounds, as are known in the art. For separation of organic compounds, such as aromatic compounds, organic therapeutics, hydrocarbons, esters, ethers, amine-containing compounds, carboxylic acids, organic polymers, and the like, normal phase, ion exchange, or reversed phase supports may be appropriate.

The solvent pump is any pump capable of delivering solvent at a flow rate suitable for the selected purification method, including an isocratic or gradient format as desired. For typical peptide separations, flow rates of about 1 to 100 $\mu$L/min are generally suitable, with flow rates of about 1 to 10 $\mu$L/min being preferred for many microcolumn applications. Flow rates outside these ranges may also be appropriate, depending on the desired peak resolution and/or other factors.

Solvent pumps are selected to provide suitable flow rates and gradient properties. Such pumps are known in the art and may be obtained from various commercial suppliers. A preferred pumping system is the 140D dual syringe pump available from Perkin-Elmer, which consists of two 2.5 mL syringe pumps under the control of a gradient controller. This pump system provides pulse-less flow rates as low as about 1 $\mu$L/min at pressures as high as 3000 psi. Further description of a pump useful for the present invention can be found in copending U.S. application Ser. No. 08/414,663 filed Mar. 31, 1995, the disclosure of which is incorporated herein by reference.

Tubing connections are preferably configured to minimize dead volume in the system and to be inert with respect to the solvents and analytes used in the separation. Fused silica transfer lines, "TEFLON" tubing, and stainless steel are suitable for most applications, although other materials may be used.

The sample injector is likewise conventional. For example, a 112A Sample Injector from Perkin-Elmer may be used. The sample loop for loading the sample onto the column typically holds a sample volume of 1 to 50 µL, and preferably 5 to 25 µL, according to the amount and concentration of the analytes to be measured.

The eluate monitoring means is any detector appropriate for monitoring the analytes of interest. The detector operates according to any detection technique that is appropriate for the analytes of interest. Typical detection methods include UV-visible absorption, fluorescence, chemiluminescence, CCD, radioisotopic detection, and ionization detection (electrical conductance), for example.

The analytes of interest are detected on the basis of an intrinsically detectable signal, or may be derivatized with a label which confers a desired type of detectability. Various methods for labeling analytes with detectable moieties are well known in the art, such as radioactive isotopes, fluorescent dyes, spin labels, chemiluminescent compounds, and the like. When the analyte is a polynucleotide, labeling by hybridization with a labeled probe is also contemplated.

Detection by UV-visible absorbance spectroscopy is accomplished by conventional techniques. The detector includes a light source which may be of variable or constant wavelength and bandwidth. The light beam is focussed by appropriate means, e.g., a spherical sapphire lens, to minimize dispersion. Preferably, the detector employs a standard dual-beam arrangement which allows cancellation of output fluctuations of the light source. An exemplary absorbance detector which may be used in the system is a 785 A Programmable Absorbance Detector available from Perkin Elmer, Applied Biosystems Division (Foster City, Calif.).

The detector further includes a flow cell configured to provide sufficient sensitivity for the signal to be detected or measured. Conveniently, the flow cell is a U-shaped flow cell of selected path length and cross-section, which allows an illuminating light source to pass down the path of fluid flow through the bottom arm of the U-cell. Typical path lengths are from about 2 to 10 mm. Typical cross-sections (inner diameters) are generally from about 25 to about 200 µm. It will be appreciated that the parameters of the flow cell will depend on the properties of the analytes to be detected.

The eluate depositing means is substantially as described with reference to the blotter apparatus described in Section II.

The control unit of the system operatively connects the monitoring and depositing means for controlling the flow rate and volume of deposited microdrops. The control unit may be prepared using standard microprocessor components and design. The control unit accepts data input from the user regarding the start of sample collection and the start of signal recordation, as well as chart recorder speed and lateral speed of the deposition head relative to the adsorbent layer. The controller also regulates the reciprocating rate of the head relative to the adsorbent layer and the duration of contact between the adsorbent layer and the capillary outlet in each contact cycle.

The control means may also be operable to change the deposition rate and microdrop deposition volume in response to different peak patterns detected by the monitoring means. For example, the control means can be programmed to select, for analysis of selected components, those drops and only those drops that contain those components in pure form, thus maximizing the amount of pure material available for analysis and conserving the collection layer. The control means can also reduce droplet size and increase deposition rate to improve separation of any component during a run. Finally, the control means can be programmed to coordinate eluate monitoring and microdrop deposition to minimize peak-component overlap in the deposited microdrops.

IV. Method

The present invention includes a method of collecting one or more molecular components derived from a mixture of components. In the method, a mixture of molecular components is separated on a capillary liquid chromatography column. The component-containing eluate from the column is deposited as a series of discrete, defined-volume microdrops along a region of an adsorbent collection layer, using an apparatus or system as described above. The collected components in the collection layer may then be analyzed by selected analytical techniques. In this regard, the invention also includes a method of analyzing one or more molecular components in a mixture of components, as outlined above.

In the method of the present invention, the collected sample components may be analyzed by a variety of methods. For protein samples, individual protein components (e.g., intact proteins or proteolysed peptide fragments) can be excised from the collection layer using a razor blade, for transfer to a protein sequencer. In this regard, it is particularly useful to have obtained a chromatogram of the eluate to allow alignment of the eluate with the collection layer to identify the positions of the separated components on the collection layer, as illustrated in the Examples below. Such protein samples may also be analyzed while still bound to the collection layer, e.g., by immunoassay to detect the presence or amount of selected analytes, or in a binding assay with a labeled receptor or ligand which is binds the analyte.

Collected sample components may also be transferred by blotting or overlay with solid gel layers and the like (e.g., polyacrylamide gels) which contain enzymes substrates, immunoassay components, or other suitable reagents for producing a signal in the presence of the selected analytes. For examples, Northern, Southern, and western blotting techniques may be used as appropriate, according to methods known in the art (e.g., Sambrook, 1989).

The features of the invention will be further appreciated from discussion of Examples 1 to 4 below, with reference to FIGS. 5 to 8.

Figure 5:
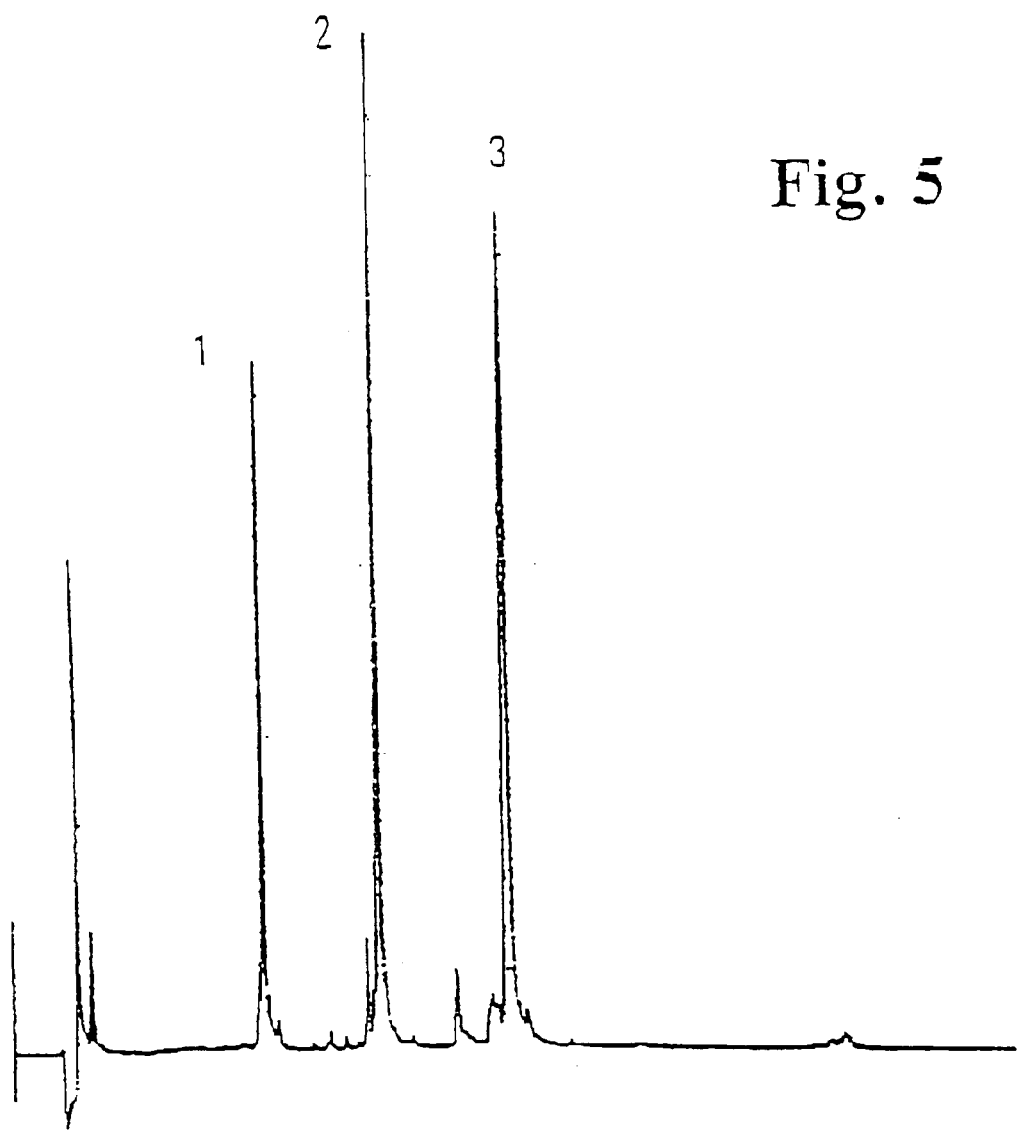
FIG. 5 shows a chromatogram of a sample mixture containing ribonuclease A (peak 1), lysozyme (peak 2), and apomyoglobin (peak 3)

FIG. 5 illustrates use of the invention for the collection and analysis of polypeptides. As detailed in Example 1, a protein mixture containing 0.3 µg each of ribonuclease A, lysozyme, and apomyoglobin in 0.1% TFA was chromatographed using a C-18 microcolumn with an acetonitrile gradient, and the effluent was collected on a PVDF membrane. When chromatography was complete, the PVDF membrane was dried, washed with methanol and water, and soaked for 1 to 2 minutes in a protein staining solution consisting of 0.05% (w:v) copper phthalocyanine-3,4'4"4'"-tetrasulfonic acid tetrasodium salt (CPTS) in 0.1% TFA. After staining, the membrane was destained with water and allowed to dry. The three stained spots, which corresponded to the expected protein peaks on the chromatogram, were excised from the membrane and transferred to a sequencer cartridge for sequencing. As seen from Table 1 in Example 1, initial sequencing yields were high, ranging from 56% to 62%.

Examples 2 to 4 illustrate the usefulness of the invention for analysis of peptide fragments from a range of proteins. In Example 2, a tryptic digest of BSA (10 pmol) was chromatographed on a C-18 column with a shallower acetonitrile gradient. As a visible standard, the sample included methyl violet base B ("dye marks") which produced a triplet of peaks that eluted after the last of the tryptic fragments (see chromatogram in FIG. 6). Regions of the PVDF membrane corresponding to six selected peaks (numbered 1 to 6 in FIG. 6) were excised and subjected to N-terminal sequence analysis. As tabulated in Example 2, initial sequencing yields ranged from about 21% to about 50%, depending roughly on the length of the peptide sequenced (wash-out effect).

Figure 7A:
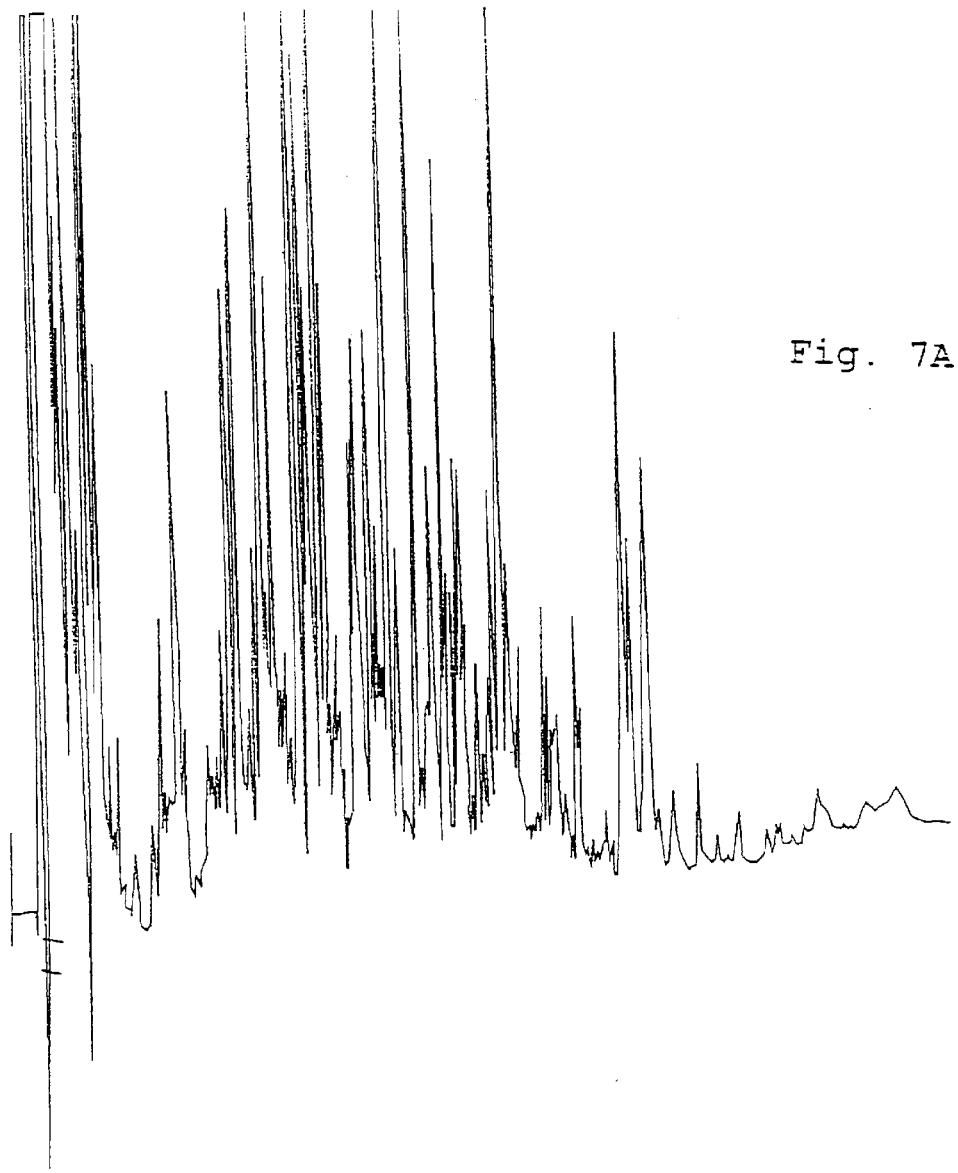
FIG. 7A shows a chromatogram of a tryptic digest of t-PA.
Figure 7B:
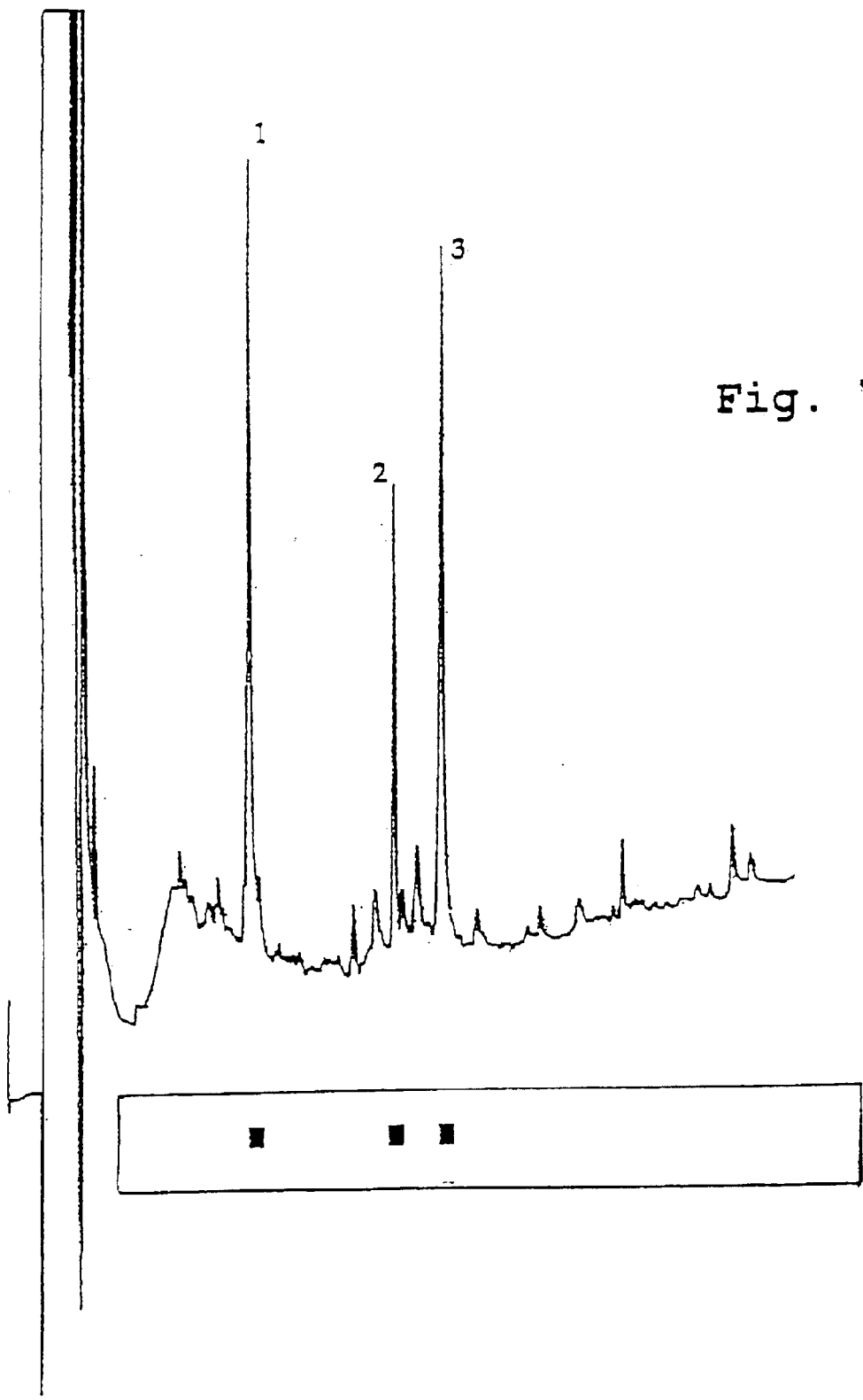
FIG. 7B shows a chromatogram of glycopeptides isolated by lectin affinity binding.

Example 3 describes purification and collection of glycopeptides from the glycoprotein t-PA (tissue plasminogen activator). Following tryptic digestion of t-PA, glycopeptides were isolated by lectin affinity binding (Hsi et al., 1993). Chromatograms of the tryptic digest and the three affinity-purified glycopeptides are shown in FIGS. 7A and 7B. Initial sequencing yields were about 30–40% for 100 pmol loaded sample, indicating that the cLC-blotter has excellent sample capacity. The sequencing results showed that the sequences are identical to published sequence data for t-PA (Spellman, 1989). Further, each glycopeptide contained a consensus sequence pattern for N-linked glycosylation, —N—X—S/T, where X is any amino acid and N is glycosylated, which explained the blank cycles observed for residues in the N position in each of the sequenced peptides.

Figure 8:
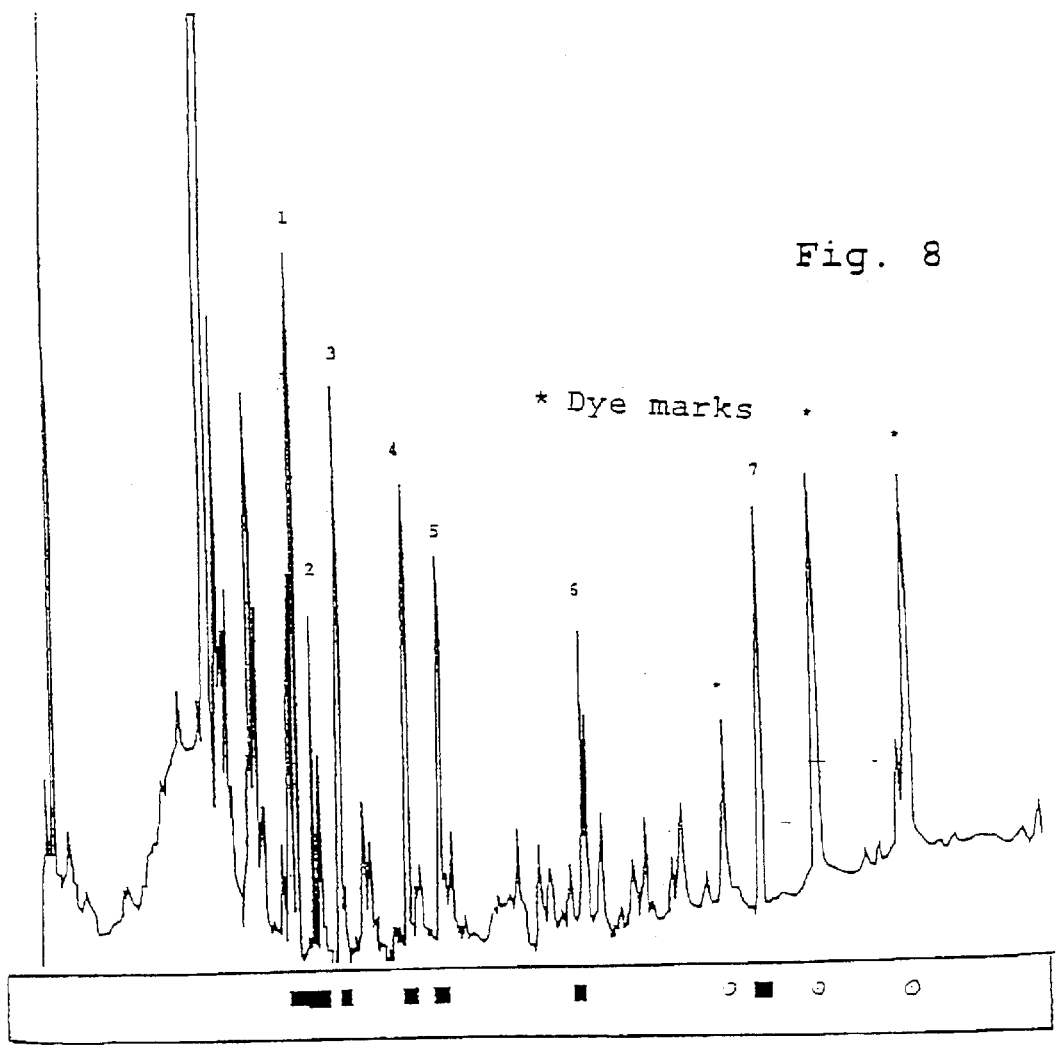
FIG. 8 shows a chromatogram of a tryptic digest of apomyoglobin.

Isolation and analysis of tryptic peptides from apomyoglobin is described in Example 4, with a chromatogram of the fragments shown in FIG. 8. Two peaks, peak 4 (residues 134–139) and peak 6 (residues 64–77) were sequenced, giving high initial yields of 42% and 63%, respectively.

The following examples are intended to illustrate but not limit the invention.

EXAMPLES

Materials and Methods

Chemicals. Bovine serum albumin (BSA), apomyoglobin, reduced "TRITON X-100", CAPS and "CON A-SEPHAROSE 4B" were purchased from Sigma Chemical Co. (St. Louis, Mo.). Trypsin was purchased from Promega (Madison, Wis.). Human tissue plasminogen activator (t-PA) was purchased from Cal Biochem (San Diego, Calif.). Dye marker methyl violet base B was purchased from Aldrich (Milwaukee, Wis.). Pre-cast Tris-Tricine gels were purchased from Novex (San Diego, Calif.). HPLC solvents, TFA (trifluroacetic acid) and "POLYBRENE PLUS" were from Perkin-Elmer, Applied Biosystems Division (Foster City, Calif.).

Peptide Mapping. BSA or t-PA in 0.1 M ammonium bicarbonate was digested with trypsin at an enzyme/substrate mass ratio of 1:50 for 10 to 16 hr. Both proteins were reduced and alkylated with β-mercaptomethanol/4-vinylpyridine as described by Hawke and Yuan (1988) prior to digestion. Digestion of apomyoglobin was carried out in 100 mM Tris/HCl buffer containing 10% acetonitrile and 1% reduced Triton X-100.

Preparation of t-PA Glycopeptides. Glycopeptides from t-PA were prepared using a micro batch lectin affinity binding technique described by Hsi et al. (1993). In brief, a tryptic digest of t-PA was mixed with Con A Sepharose 4B in a 1 ml Eppendorf tube for 30 min. After washing with Tris-HCl buffer to remove all unbound peptides, the bound glycopeptides were released with α-methyl mannoside. The resulting glycopeptides, after separation and blotting on the cLC-microblotter, were sequenced on a Procise-HT Sequencer.

Capillary Liquid Chromatoaraphy System. A sample purification and collection system was assembled as illustrated in FIG. 4. The system included a 140D dual syringe pump (2.5 mL syringe volumes) equipped with a T-mixer; a 112A Injector (Rheodyne 8125) equipped with a 5–20 $\mu$L sample loop; a C-18 reversed phase column (150 mm×0.5 mm I.D., 5 $\mu$m particles); a 785A Programmable Absorbance Detector equipped with a 30 nL, 6 mm path-length U-shaped flow cell, with signal output directed to a strip chart recorder; and a blotter apparatus equipped with a push-pull solenoid substantially as illustrated in FIGS. 1 and 2, the solenoid being held by a drive arm for lateral movement over the blotter tray. All connective tubing (fused silica) between the pump and the detector flow cell had an internal diameter (I.D.) of 50 $\mu$m and an outer diameter (O.D.) of about 370 $\mu$m. Movement of the solenoid was controlled by a controller which coordinated the lateral speed of the solenoid and the frequency and duration of contact of the outlet end of the capillary tube with the PVDF membrane.

The capillary tubing connecting the flow cell to the system outlet (i.e., the end protruding from the blotter solenoid) had an I.D. of 30 $\mu$m. The tip of the capillary tubing protruding from the solenoid was sleeved with a ¼ inch length of 0.012 inch×0.009 inch "TEFLON" tubing which was made flush with the protruding end of the capillary tubing.

Prior to each run, the adsorbent tray in the blotter apparatus was loaded with a strip of filter paper (Biorad Cat. No. 170-3956). The filter paper was thoroughly wetted with deionized water. After the tray was tilted to remove excess water from the filter paper, a PVDF membrane of the same size as the filter paper was wetted with methanol and then placed directly over the wet filter paper. A dry strip of filter paper was then laid on top of the PVDF membrane, and a gloved finger was run along the top of the filter paper from one end to the other to remove air pockets between the PVDF membrane and the underlying filter paper. The top strip of filter paper was then removed, and the blotter tray was placed in the blotter housing of the apparatus.

After sample loading and initiation of the solvent gradient program by the controller, the chart recorder and solenoid were activated so that the chart paper and solenoid drive arm moved at the same speeds. The outlet end protruding from the solenoid was periodically contacted with the PVDF membrane as the solenoid moved laterally across the membrane.

When the chromatographic separation was complete, the PVDF membrane was removed from the blotter tray with a tweezers and was allowed to air-dry on a "KIMWIPE" tissue. The dried membrane was then aligned with the chromatogram on the chart paper, and membrane regions corresponding to peaks of interest were excised using a razor blade and were used immediately for protein sequencing or were sealed in an "Eppendorf" tube and refrigerated for later analysis.

For the examples below, the blotter speed and strip chart recorder speed were each 1 mm/min; contact time of the tip of the capillary outlet with the PVDF membrane was about 1.8 sec per cycle, with a total cycle time of 2 sec per cycle; solvent A=0.1% TFA in water, solvent B=0.085% TFA in acetonitrile; and absorbance wavelength was 210 nm at 1 AUFS (Example 1) or 0.1 AUFS (Example 2). Collected sample components were typically 1 to 2 mm in diameter based on protein staining.

Sequence Analysis. N-terminal sequence analysis was conducted using an Applied Biosystems 473 or Procise-HT Sequencer. All peptides were treated with 1–2 $\mu$L of "POLYBRENE PLUS" solution prior to loading in the sequencer. The "POLYBRENE" solution was made by mixing 1 part of "POLYBRENE PLUS" (100 mg/ml in water), 1 part of 0.1%

TFA and 2 parts of MeOH. Total "POLYBRENE" applied was 25–50 mg per excised membrane piece.

Example 1

Purification and Sequencing of Three Proteins

The system described above was used to purify and collect a sample consisting of 0.3 µg each of ribonuclease A, lysozyme, and apomyoglobin in 0.1% TFA. The elution gradient was 15%–65% B over 75 min at a flow rate of 4 µL/min. Once chromatography was complete, the PVDF membrane was dried and then wetted with methanol for a few seconds followed by deionized water for 1 minute. The PVDF membrane was then soaked for 1 to 2 minutes in a protein staining solution consisting of 0.05% (w:v) copper phthalocyanine-3,4'4"4'''-tetrasulfonic acid tetrasodium salt (CPTS) in 0.1% TFA. After staining, the membrane was destained 5 times with water (50 mL and 3 min/each wash) and allowed to dry. The stained three stained spots were excised from the membrane and transferred to a sequencer cartridge for sequencing. The resultant chromatogram and sequencing yields from the first sequencing cycles are shown in FIG. 5 and Table 1, respectively.

TABLE 1

|  | Amount Loaded (3 ug) | Init. Sequ. Yield |
| --- | --- | --- |
| Ribonuclease | 21 pmol | 56% |
| Lysozyme | 18 pmol | 62% |
| Apomyoglobin | 18 pmol | 61% |

Example 2

Purification and Sequencing of Trypsin Digest of BSA

Figure 6:
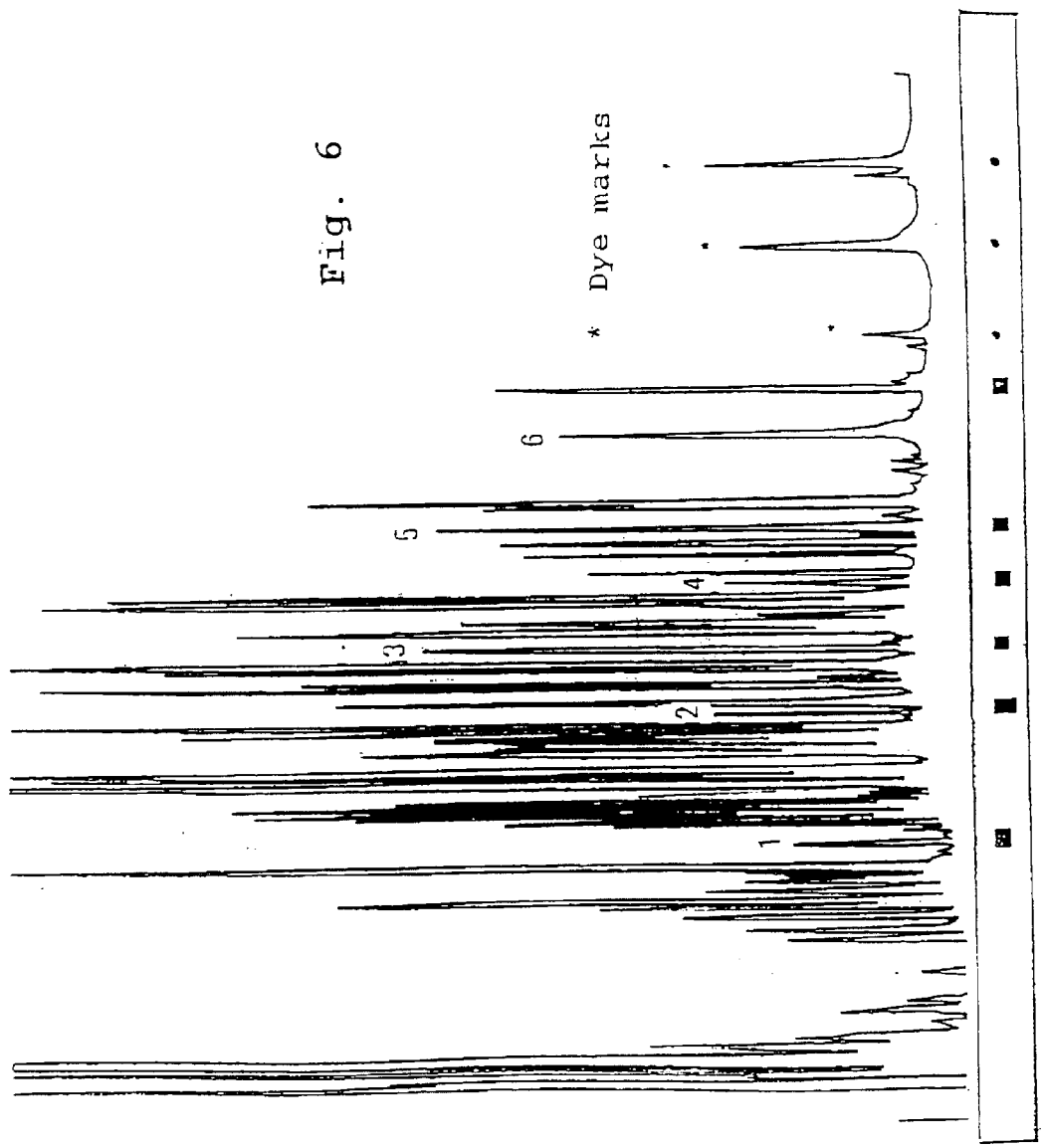
FIG. 6 shows a chromatogram of a tryptic digest of bovine serum albumin.

A tryptic digest of bovine serum albumin (BSA, 10 pmol) containing methyl violet base B was chromatographed using the system described above. Specifically, a 9 µL sample solution was mixed with 1 µL "Dye Mark" stock solution (stock=1 mg methyl violet base B per 50 mL aqueous 0.1% TFA). The elution gradient was 5%–45% B over 140 min at a flow rate of 4 µL/min. The resultant chromatogram and sequencing data for selected peaks are shown in FIG. 6 and Table 2, respectively.

TABLE 2

| Peak | Locations in BSA (Residue Number) | Init. Sequ. Yield |
| --- | --- | --- |
| 1 | 310–318 | 21% |
| 2 | 161–167 | 24% |
| 3 | 66–75 | 40% |
| 4 | 319–336 | N/A* |
| 5 | 569–580 | 49% |
| 6 | 45–65 | 50% |

*Not available.

Example 3

Purification and Sequencing of t-PA Glycopeptides

Glycopeptides from a tryptic digest of t-PA were chromatographed using the system described above and then sequenced. Chromatograms of the digest and the three resolved glycopeptides are shown in FIGS. 7A and 7B, respectively. Initial sequencing yields were about 30–40% for 100 pmol loaded sample. With reference to FIG. 7B, the three glycopeptides corresponded to residues 441–449 (peak 1), 163–189 (peak 2), and 102–124 (peak 3), as determined by sequence analysis.

Example 4

Purification and Sequencing of Apomyoglobin

A tryptic digest of apomyoglobin (1 pmol) containing methyl violet base B was chromatographed using the system described above. A chromatogram is shown in FIG. 8. Initial sequencing yields for peak 4 (residues 134–139) and peak 6 (residues 64–77) were 42% and 63%, respectively.

Although the invention has been described by way of illustration and example for purposes of clarity and understanding, it will be appreciated that various modifications can be made without departing from the invention. All references and patent applications cited above are incorporated herein by reference.

It is claimed:

1. A blotting apparatus for collecting one or more molecular components derived from a mixture of components, comprising a capillary liquid chromatography column, an adsorbent collection layer, and means for depositing component-containing eluate from a capillary liquid chromatography column as a series of discrete, defined-volume microdrops, along a region of the adsorbent collection layer.

2. The apparatus of claim 1, further including means for monitoring eluate from a capillary liquid chromatography column to detect the presence of separated components in the eluate, and a control unit operatively connecting the monitoring and depositing means for controlling the flow rate and volume of deposited microdrops.

3. The apparatus of claim 1, wherein the collection layer is immobile, and said depositing means include a deposition head, for depositing said eluate on the collection layer, capable of reciprocating toward and away from a position of contact with the collection layer while the deposition head is moved laterally relative to the collection layer.

4. The apparatus of claim 1, wherein said depositing means includes (i) a deposition head, for depositing column eluate on the collection layer, said deposition head being capable of reciprocating toward and away from a position of contact with the collection layer, and (ii) means for moving said adsorbent layer laterally relative to the deposition head.

* * * * *